United States Patent
Rouse et al.

(10) Patent No.: US 7,048,768 B1
(45) Date of Patent: May 23, 2006

(54) MULTI-FUNCTION BODY-POWERED PROSTHETIC WRIST UNIT AND METHOD

(76) Inventors: John Hoover Rouse, Rt. 5, Box 109, Angleton, TX (US) 77515; Ronald Hayden Farquharson, 9483 County Rd. 628, Brazoria, TX (US) 77422; Charles Glenn Betts, 53 Plantation Ct., Lake Jackson, TX (US) 77566

( * ) Notice: Subject to any disclaimer, the term of this patent is extended or adjusted under 35 U.S.C. 154(b) by 19 days.

(21) Appl. No.: 10/768,617

(22) Filed: Jan. 30, 2004

(51) Int. Cl.
*A61F 2/58* (2006.01)
(52) U.S. Cl. .................................................. 623/61
(58) Field of Classification Search ............... 623/61, 623/62, 57, 24, 25
See application file for complete search history.

(56) References Cited

U.S. PATENT DOCUMENTS

| | | | | |
|---|---|---|---|---|
| 1,362,793 A | * | 12/1920 | Hirsch | 623/62 |
| 2,457,316 A | * | 12/1948 | Northrop et al. | 623/62 |
| 3,900,900 A | * | 8/1975 | Horvath | 623/61 |
| 4,010,495 A | * | 3/1977 | Horvath | 623/61 |
| 4,068,763 A | * | 1/1978 | Fletcher et al. | 414/4 |
| 4,156,945 A | * | 6/1979 | May | 623/61 |
| 4,370,791 A | * | 2/1983 | Wilson | 29/407.1 |
| 2004/0015240 A1 | * | 1/2004 | Archer et al. | 623/62 |

FOREIGN PATENT DOCUMENTS

| | | | |
|---|---|---|---|
| GB | 2236054 A | * | 3/1991 |
| GB | 2278281 | * | 11/1994 |
| WO | WO03017881 A1 | * | 3/2003 |

* cited by examiner

*Primary Examiner*—Alvin J. Stewart
(74) *Attorney, Agent, or Firm*—Kenneth A. Roddy

(57) ABSTRACT

A multi-function body-powered prosthetic wrist unit that is attachable to the end of a prosthesis on an arm and provides over 270° of smooth pronation and supination rotation with a plurality of indexed rotation locking positions, wrist flexion and extension from 0 to 50° with three locking positions, and a quick disconnect connection for attachment of a variety of terminal devices thereto. Integral cable release assemblies provide body powered release for pronation and supination rotation and flexion and extension. Cable operated locks can be retracted or released passively by body-powered harnessing, and allow momentary (pull-to-release) or alternating (pull/relax) locking functions.

18 Claims, 3 Drawing Sheets

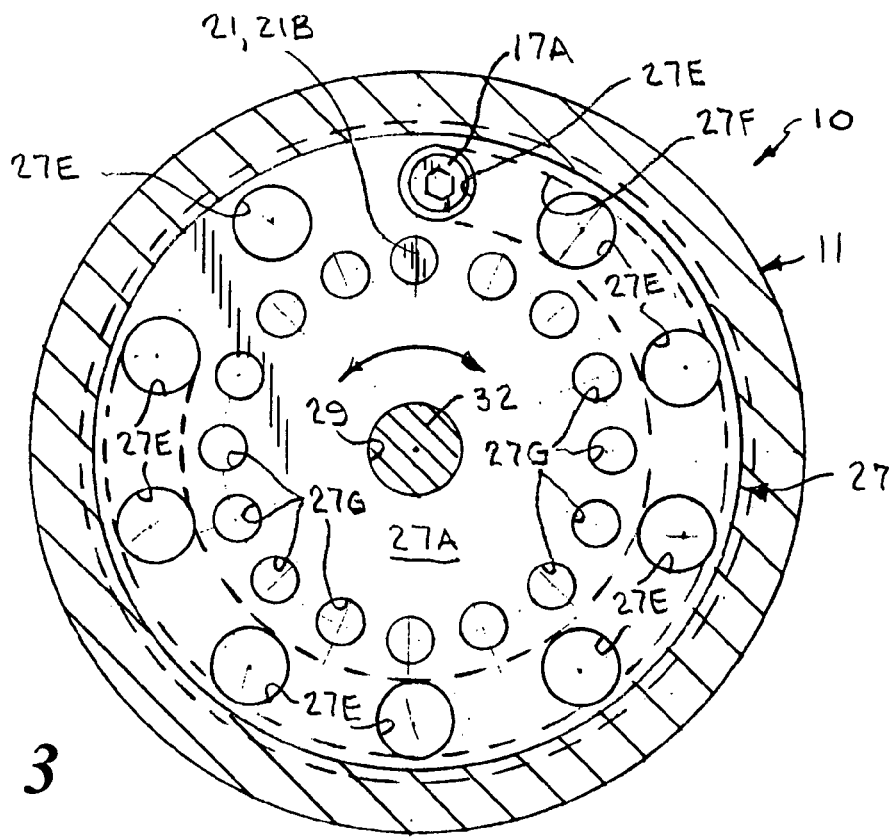
*Fig. 3*
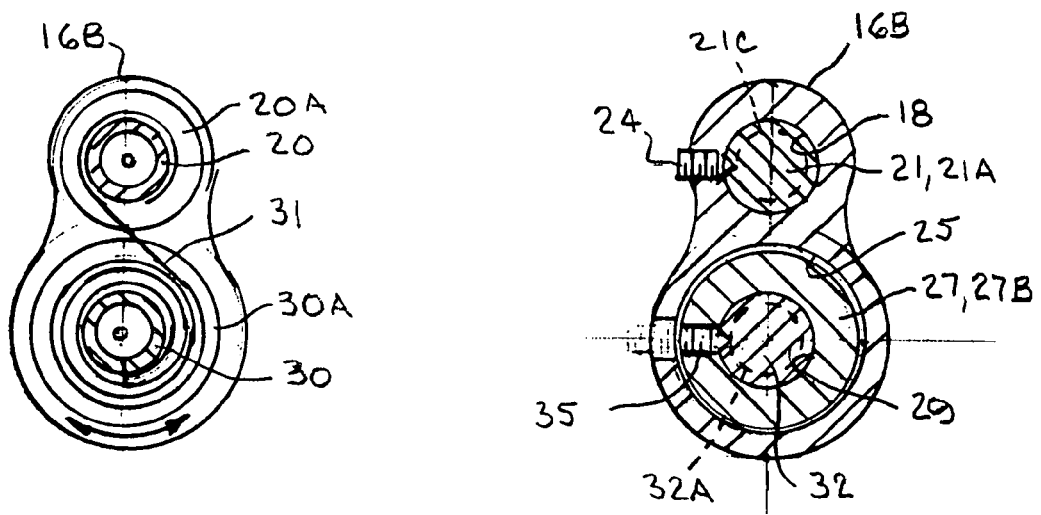
*Fig. 5*  *Fig. 4*

MULTI-FUNCTION BODY-POWERED PROSTHETIC WRIST UNIT AND METHOD

BACKGROUND OF THE INVENTION

1. Field of the Invention

This invention relates generally to the field of prosthetic hand and arm attachments, and more particularly to a multi-function body-powered prosthetic wrist unit that provides over 270° of smooth pronation and supination rotation with a plurality of locking positions, wrist flexion and extension from 0 to 50° with several locking positions, and a quick disconnect connection for attachment of a variety of terminal devices, such as hooks, electric hands, tools, implements, and other specialty terminal devices, thereto.

2. Background Art

Throughout this disclosure the expression "terminal device" is used in the ordinary vernacular of arm prostheses as a device (such as a hook, hand, electric hand, tool or implement) added to the most distal end of an arm prosthesis, for example at a wrist location. In the context of the present wrist unit invention, the terminal device is the device that is attached to the wrist unit. The phrase "active control" refers to motion between adjacent parts that is achieved by body powered harnessing. The phrase "passive control" refers to motion between adjacent parts that is achieved by direct application of external forces.

There have been a large number of prosthetic devices for use by amputees who have lost at least one or both hands, or one or both arms. Many of the devices are body-powered and some are driven, or at least assisted, by electrical, myoelectrical, and/or pneumatic means.

Most extremity prostheses currently in use have a terminal device (such as a hand or hook) controlled either by movements of a shoulder harness transmitted via a cable (i.e. body powered), or by myoelectric control (i.e., motors triggered by the contraction of muscles in the residual limb). However, conventional actively and passively controlled prosthetic devices have only one or two controlled degrees-of-motion, and provide limited ability to grasp, properly position, and manipulate the terminal device.

Thus, there exists a need to provide a prosthetic wrist device having improved control of multiple degrees of pronation and supination rotation, wrist flexion and extension, with a plurality of locking positions, along with a provision for quick and easy attachment of a variety of terminal devices, such as hooks, electric hands, tools, implements, and other specialty terminal devices.

Perez, U.S. Pat. No. 3,490,078 discloses a flexible sleeve for a forearm stump which has a threaded female member at the end of the sleeve into which can be threaded a handle of a tool.

Bengtson, U.S. Pat. No. 3,802,302 discloses a tool holding prosthetic device having a threaded connector devices for attaching various tools and shows the use of a detent ball.

Winter, U.S. Pat. No. 3,942,194 discloses a device for attaching to a hand to which an implement can be removably fastened.

Adkins, U.S. Pat. No. 4,661,113 discloses a device which is attachable to an amputee's prosthesis to enable the amputee to swing a golf club or other device which requires swinging.

Keith, U.S. Pat. No. 4,944,765 discloses an artificial arm prosthetic drive device for holding a rotatable tool.

Norton et al, U.S. Pat. No. 5,163,966 discloses a prosthetic limb having a means for grasping and holding a bar or tubular member.

Farquharson et al, U.S. Pat. No. 5,464,444, commonly owned with the present invention, and hereby incorporated herein by reference, discloses a terminal device that is attachable to the end of a prosthesis on an arm and serves as a universal attachment site for a variety of tools and implements designed to mate with the device.

The present invention is distinguished over the prior art in general, and these patents in particular by a multi-function body-powered prosthetic wrist unit that is attachable to the end of a prosthesis on an arm and provides over 270° of smooth pronation and supination rotation with a plurality of indexed rotation locking positions, wrist flexion and extension from 0 to 50° with three locking positions, and a quick disconnect connection for attachment of a variety of terminal devices thereto. Integral cable release assemblies provide body powered release for pronation and supination rotation and flexion and extension. Cable operated locks can be retracted or released passively by body-powered harnessing, and allow momentary (pull-to-release) or alternating (pull/relax) locking functions.

SUMMARY OF THE INVENTION

It is therefore an object of the present invention to provide a multi-function body-powered prosthetic wrist unit for attachment to the distal end of an arm prosthesis that is compact in size, very light weight, and smooth in operation.

It is another object of this invention to provide a multi-function body-powered prosthetic wrist unit that enables five-functions, including multiple degrees of pronation and supination rotation, wrist flexion and extension, and a quick disconnect provision for quick and easy attachment of a variety of terminal devices, such as hooks, electric hands, tools, implements, and other specialty terminal devices.

Another object of this invention is to provide a multi-function body-powered prosthetic wrist unit that allows smooth pronation and supination rotation through a large angle of rotation about a longitudinal axis extending through the wrist unit, and has a plurality of selective indexed rotation locking positions at which it may releasably locked by the wearer.

Another object of this invention is to provide a multi-function body-powered prosthetic wrist unit having a quick disconnect member that pivots about an axis transverse to a longitudinal axis extending through the wrist unit and allows for quick attachment and release of a variety of terminal devices thereto, and which has selective pivot locking positions at which it may releasably locked by the wearer.

A further object of this invention is to provide a multi-function body-powered prosthetic wrist unit that allows for smooth pronation and supination rotation and flexion and extension motions and has release mechanisms that can be actuated passively by body-powered harnessing.

A still further object of this invention is to provide a multi-function body-powered prosthetic wrist unit that is simple in construction, inexpensive to manufacture, and rugged and reliable in operation.

Other objects of the invention will become apparent from time to time throughout the specification and claims as hereinafter related.

The above noted objects and other objects of the invention are accomplished by a multi-function body-powered prosthetic wrist unit that has a rear member having a back end configured to be releasably attached to the terminal end of an arm prosthesis and a front member rotatably connected the rear member to rotate relative thereto about a longitudinal axis extending through said wrist unit to provide over 270° of smooth pronation and supination rotation and has a plurality of indexed rotation locking positions. The front member of the wrist unit has a quick disconnect connection for attachment of a variety of terminal devices thereto which pivots about an axis transverse to the longitudinal axis to provide flexion from 0 to 50° with three locking positions. Retractable rotation and flexion locking pins connected with respective control cables can be retracted or released passively by body-powered harnessing, and allow momentary (pull-to-release) or alternating (pull/relax) locking functions.

BRIEF DESCRIPTION OF THE DRAWINGS

FIG. 3 is a transverse cross section view of the a multi-function body-powered prosthetic wrist unit taken along line 3—3 of FIGS. 1 and 2, showing the plurality of indexed rotation locking holes in the flange of the rotation locking member.

FIG. 4 is a transverse cross section view through the locking pin housing taken along line 4—4 of FIG. 2, showing the set screw and licking pin arrangement.

FIG. 5 is a transverse cross section view taken along line 5—5 of FIG. 2, showing the torsion spring between the sleeve of the rotation locking member and the locking pin housing.

DESCRIPTION OF THE PREFERRED EMBODIMENTS

Figure 1:
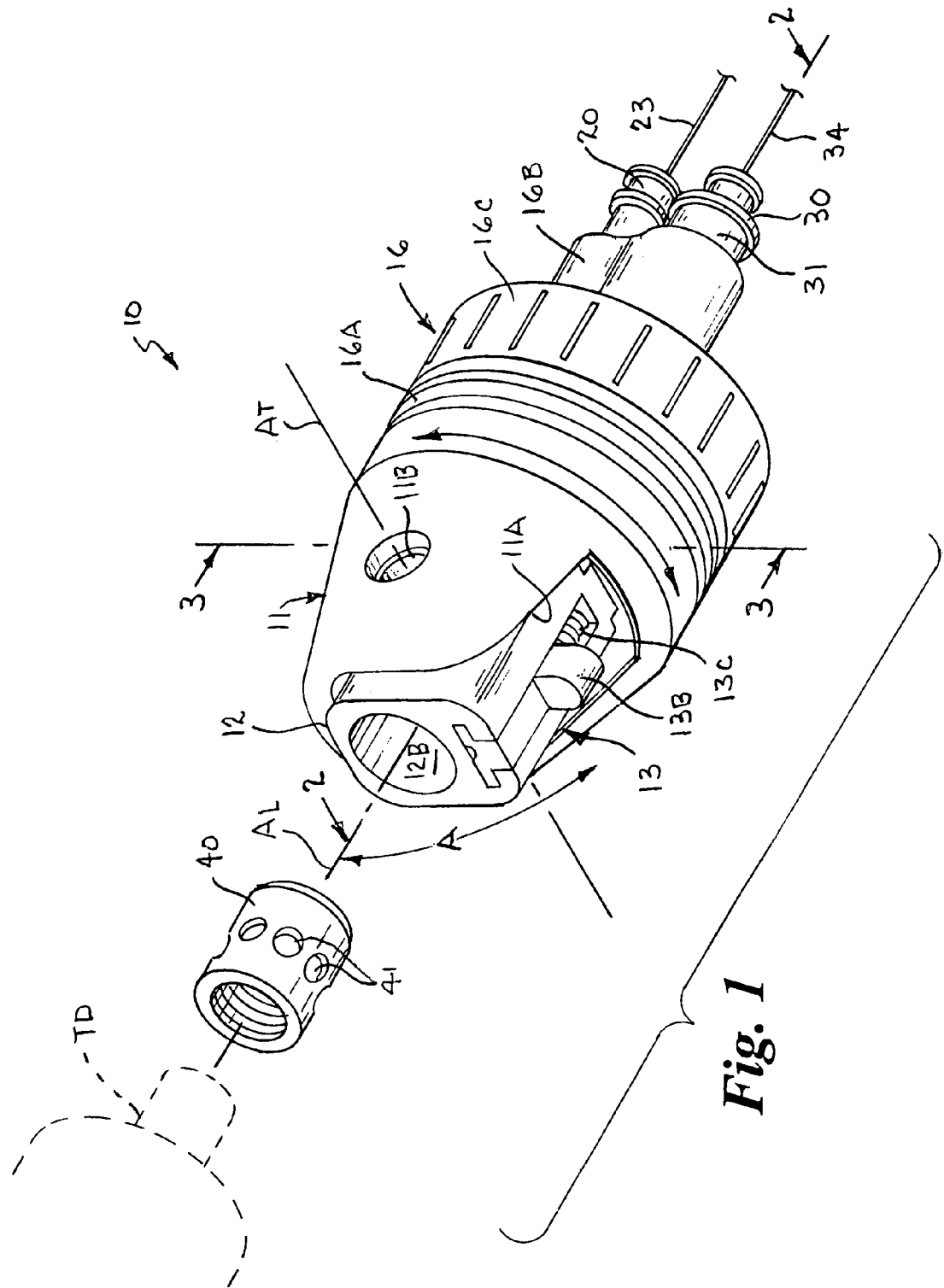
FIG. 1 is a perspective view of a multi-function body-powered prosthetic wrist unit in accordance with the present invention.
Figure 2:
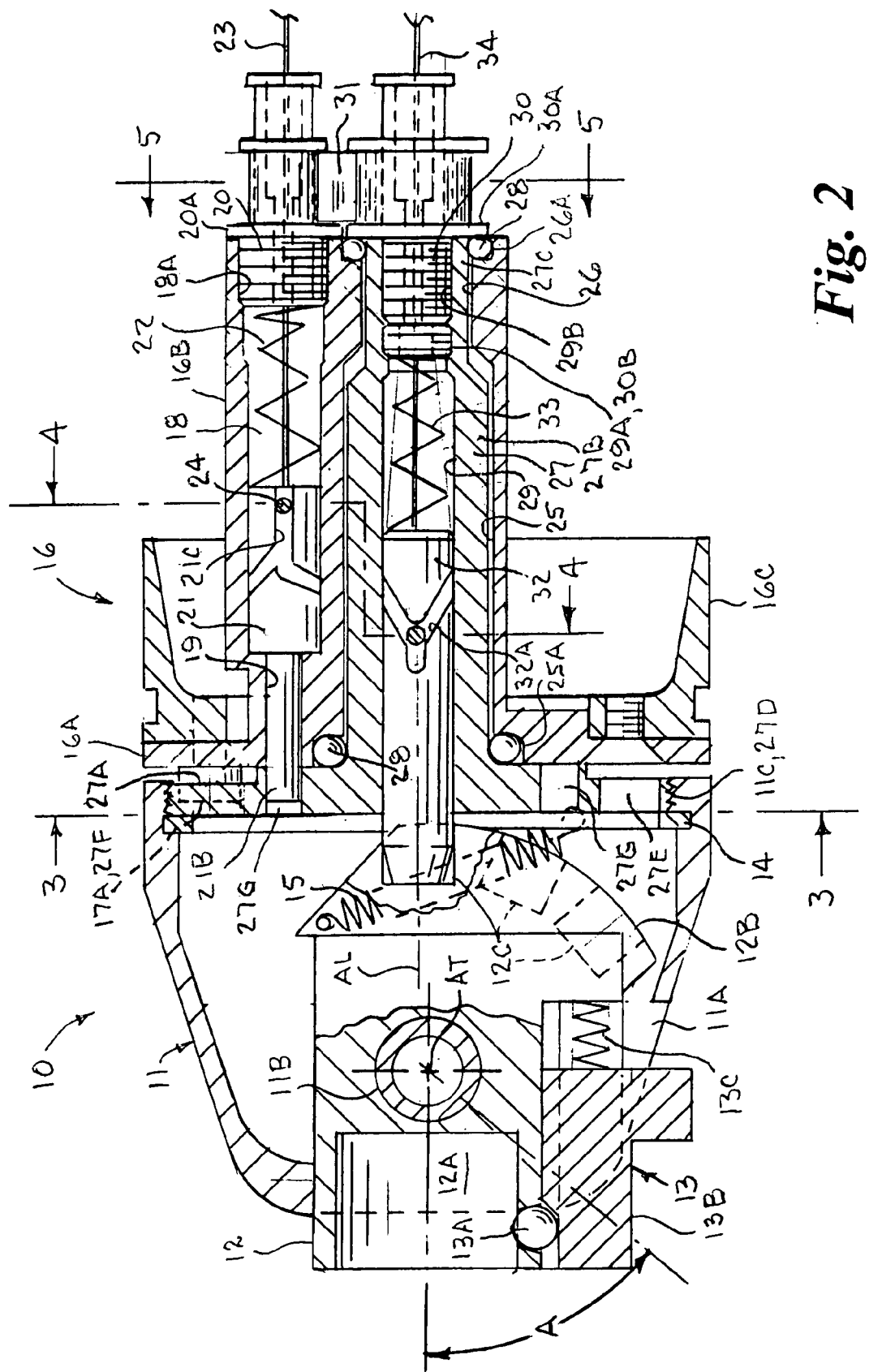
FIG. 2 is a longitudinal cross section view of the multi-function body-powered prosthetic wrist unit taken along line 2—2 of FIG. 1.

Referring to the drawings by numerals of reference, there is shown in FIGS. 1, 2, 3 and 4, a preferred embodiment of the multi-function body-powered prosthetic wrist unit 10 in accordance with the present invention. The wrist unit 10 has a first generally conical front member 11 rotatably connected at its rear end with a second generally cylindrical rear member 16 with a back end configured to be releasably attached to the end of an arm prosthesis. The front member 11 rotates relative to the rear member 16 about a longitudinal axis AL extending through the wrist unit 10.

The conical front member 11 has a slotted opening 11A extending partially across its front end and a distance rearward along one side thereof. A generally rectangular quick disconnect connector 12 is pivotally mounted in the slotted opening 11A by a hollow pivot pin 11B extending transversely through the conical front member 11 and rear portion of the quick disconnect connector. As described hereinafter, the quick disconnect connector 12 is pivotally mounted in the opening 11A to pivot at an angle "A" of from 0° to about 50° about an axis AT transverse to the longitudinal axis.

The quick disconnect connector 12 has a cylindrical cavity 12A extending a distance inwardly from its front end that functions as a receptacle for receiving the proximal end of various terminal devices TD, and an outer facing side of the quick disconnect connector is fitted with a releasable locking mechanism 13 for releasable attachment of a variety of terminal devices thereto. In the illustrated example, the locking mechanism 13 is a quick-disconnect mechanism having a detent ball 13A extensible partially through a hole in the side wall of the cylindrical cavity 12A and a retractable plunger 13B. The plunger 13B is biased to a forward extended position by a compression spring 13C to urge the ball into engagement with an indentation or hole 41 on a cylindrical adapter or insert 40 which is attached to the terminal device TD, or a cylindrical end portion of a terminal device. It should be understood that other types of easily released retaining means may be used. The back end of the quick disconnect connector 12 has an arcuate curved portion 12B with three locking holes 12C formed therein.

The open back end of the front member 11 has internal threads 11C that terminate in a snap ring groove in which a snap ring 14 is mounted. A tension spring 15 having one end attached to the snap ring 14 and its other end attached to the arcuate curved portion 12B of the quick disconnect connector 12, urges the quick disconnect connector to a normally straight position with its cavity 12A parallel with the longitudinal axis AL of the wrist unit 10. In this position, a first one of the three holes 12C in the arcuate curved portion 12B of the quick disconnect connector 12 is parallel with the longitudinal axis of the wrist unit.

The generally cylindrical rear member 16 has a flat circular flange 16A at a front end with a generally rectangular locking pin housing 16B extending rearward a distance from the circular flange portion. A cylindrical cup-shaped lamination ring 16C is attached to the back side of the flange 16A by screws 17. At least one of the screws 17 is an allen head cap screw 17A. In the illustrated example, the lamination ring 16C has an outer periphery configured to be engaged in a socket at the distal end of an arm prosthesis.

A locking pin bore 18 extends forwardly from the rear end of the locking pin housing 16B and adjoins a shorter smaller diameter bore 19 which extends through the flat circular flange 16A of the housing. The rear portion of the bore 18 is provided with internal threads 18A and a plug 20 having a radial flange 20A is threadedly engaged therein. A retractable rotation locking pin 21 having a larger diameter rear portion 21A and a smaller diameter front portion 21B is slidably disposed in the bore 18 of the locking pin housing 16B with the smaller diameter front portion received in the smaller bore 19. A compression spring 22 is engaged between the back end of the rotation locking pin 21 and the plug 20 to normally urge the rotation locking pin forward to a locking position. A rotation control cable 23 is attached at one end to the back end of the rotation locking pin 21 and extends through the spring 22 and the plug 20 engaged in the back end of bore 18. The other end of the rotation control cable 23 is attached to a harness worn by the amputee (conventional in the art, and therefore not shown). The larger diameter rear portion 21A of the rotation locking pin 21 is provided with a circumferential cam groove 21C. The nose of a set screw 24 mounted in the side wall of the bore 18 rides in the cam groove 21C (FIG. 4).

A larger central bore 25 disposed parallel with, and spaced a distance from the locking pin bore 18 extends through the flat circular flange portion 16A of the cylindrical rear member 16 and a distance rearwardly through the locking pin housing 16B and adjoins a shorter smaller diameter bore 26 which extends through the rear end of the housing and is surrounded by a counterbore 26A. A counterbore 25A in the flange portion 16A surrounds the central bore 25.

A rotation locking member 27 having a flat circular flange 27A at a front end and a tubular sleeve portion 27B extending rearwardly therefrom and terminating in a smaller diameter rear portion 27C is rotatably mounted in the central bore 25, with the sleeve portion 27B and smaller diameter rear portion 27C journalled therein by a ball bearings 28 received in the counterbores 25A and 26A, respectively. A central bore 29 extends through the circular flange 27A of the rotation locking member 27 and rearwardly thorough its tubular sleeve portion 27B and terminates in a first short internally threaded bore 29A near the rear end of the sleeve portion. A second short internally threaded bore 29B extends inwardly from the rear end of the sleeve portion. A plug 30 having a radial flange 30A is threadedly engaged the second bore 29B in the back end of the sleeve portion 27B of the rotation locking member 27 to retain the bearings 28. A jamb screw 30B is threadedly engaged the first bore 29A to bear against plug 30 and prevent it from becoming unscrewed during rotation of the rotation locking member 27.

The outer circumference of the circular flange 27A of the rotation locking member 27 has external threads 27D. The generally conical front member 11 carrying the quick disconnect connector 12 is attached to the rotation locking member 27 by threadedly engaging the internal threads 11C in its open back end on the exterior threads 27D of the rotation locking member flange 27A. Thus, the conical front member 11 and the quick disconnect connector 12 rotate with the rotation locking member 27 as a unit, as described hereinafter.

As best seen in FIG. 3, the flat circular flange 27A of the rotation locking member 27 has a plurality of equally spaced apart larger holes 27E therethrough radially spaced a distance from the central bore 29 in a circular pattern for installing the screws 17 which attach the circular flange 16A of the rear member 16 to the lamination ring 16C. A semicircular groove 27F is formed in the back side of the flange 27A on the same radius as the larger holes 27E. When the rotation locking member 27 is rotatably mounted in the central bore 25 of the locking pin housing 16B, the flat circular flange 27A of the rotation locking member is disposed in front of the flange portion 16A of the locking pin housing and the allen head cap screw 17A is received in the semicircular groove 27F. The flange 27A of the rotation locking member rotates relative to the flange portion 16A of the locking pin housing and the allen head cap screw 17A.

The cap screw 17A engages one end of the groove 27F to provide a stop surface to limit the rotational movement. In a preferred embodiment, the semicircular groove 27F is dimensioned to allow more than 270° of rotational travel. For example, but not limited thereto, the semicircular groove 27F may be dimensioned to provide a rotational travel limit of 290°.

Also, as best seen in FIG. 3, the flat circular flange 27A of the rotation locking member 27 has a plurality of equally spaced apart small holes 27G therethrough radially spaced a distance from the central bore 29 in a circular pattern aligned with the axis of the retractable rotation locking pin 21. The small holes 27G are sized to receive the smaller diameter front portion 21B of the rotation locking pin 21 in its extended position (described hereinafter). The number and the angular spacing of the small holes 27G is calculated to provide a plurality of indexed rotation locking positions. For example, there may be sixteen holes, equally spaced apart within a 360° circle to provide 14 indexed locking positions in a 290° rotational travel limit.

Referring additionally to FIG. 5, one end of a torsion spring 31 is engaged on the neck portion of the plug 30 at the back end of the sleeve 27B of the rotation locking member 27 and is wound thereon with its other end engaged with on the neck portion of the plug 20 at the back end of the locking pin housing 16B to allow the flat circular flange 27A of the rotation locking member, and conical front member 11 attached thereto, to rotate in one direction (clockwise or counter clockwise) against the spring force of the torsion spring.

Referring again to FIG. 2, an elongate retractable flexion locking pin 32 is slidably received in the central bore 29 of the rotation locking member 27 and a compression spring 33 is disposed between the flexion locking pin and the plug 30 to normally urge the flexion locking pin forward to a locking position. A flexion control cable 34 is attached at one end to the back end of the flexion locking pin 32 and extends through the spring 33, the jamb screw 301B, and the plug 30 engaged in the back end of the sleeve portion 27B of the rotation locking member 27. The other end of the flexion control cable 34 is attached to a harness worn by the amputee (conventional in the art, and therefore not shown). In its locking position, the front end of the flexion locking pin 32 extends through the rotation locking member flange 27A and is engaged in one of the three holes 12c in the arcuate curved portion 12B at the back end of the quick disconnect connector 12. The shank of the retractable flexion locking pin 32 is provided with a circumferential cam groove 32A. The nose of a set screw 35 mounted in the side wall of the central bore 29 of the locking pin housing 16B rides in the cam groove 32A (FIG. 4). The set screw 25 may be installed through an opening in the locking pin housing 16B.

OPERATION

Rotation (Pronation and Supination) and Locking

The retractable rotation locking pin 21 is moved rearward against the force of the compression spring 22 to a retracted position by tensioning (pulling) and then relaxing the rotation control cable 23 a first time (first pull/relax action). During the first pull stroke, the cam groove 21C moves rearward and the set screw 24 riding in the cam groove rotates the rotation locking pin 21 and when tension is relaxed, the set screw engages a stop surface in the cam groove such that the front end of the rotation locking pin is pulled away from the flange 27A of the rotation locking member 27 and is maintained flush with the flat circular flange 16A at a front end of the locking pin housing 16B.

When the rotation locking pin 21 is in the retracted position, the rotation locking member 27 including its flange 27A and sleeve portion 27B, and the attached conical front member 11 carrying the quick disconnect connector 21, may be manually rotated as a unit about the longitudinal axis AL more than 270° (for example 290°) in one direction (clockwise or counter clockwise) against the spring force of the torsion spring 31.

When the rotation locking member 27 and the attached conical front member 11 carrying the quick disconnect connector 12 is manually rotated, the small holes 27G in the rotation locking member flange 27A pass over the retracted rotation locking pin 21 until the desired rotated position is achieved, and then the rotation locking pin 21 is moved forward to an extended locking position by tensioning (pulling) and then relaxing the rotation control cable 23 a second time (second pull/relax action). During the second pull stroke, the cam groove 21C moves rearward and rotates the rotation locking pin 21 and when tension is relaxed, the set screw 24 riding in the cam groove is disengaged from the stop surface in the cam groove such that the front end of the rotation locking pin is urged forward by the compression spring 22 to be received in one of the plurality of small holes 27G in the rotation locking member flange 27A. If the front end 21B of the rotation locking pin 21, when released, engages the back surface of the flange 27A between two adjacent holes, the torsion spring 31 will rotate the flange a sufficient distance to allow the front end of the rotation locking pin to snap into the closest small hole in the flange.

Thus, the conical front member 11 carrying the quick disconnect connector 12 may be rotated about the longitudinal axis AL of the wrist unit 10 and releasably locked at selected rotated positions relative to the arm prosthesis through a range exceeding 270° (for example 290°). The plurality of indexed rotation locking positions depends upon the number and angular spacing of the small holes 27G. For example, there may be sixteen holes, equally spaced apart within a 360° circle to provide 14 indexed locking positions in the 290° rotational travel limit.

Flexion and Extension and Locking

The retractable flexion locking pin 32 is moved rearward against the force of the compression spring 33 to a retracted position by tensioning (pulling) and then relaxing the flexion control cable 34 a first time (first pull/relax action). During the first pull stroke, the cam groove 32A moves rearward and the set screw 35 riding in the cam groove rotates the flexion locking pin 32, and on the relax stroke, the set screw engages a stop surface in the cam groove to maintain the flexion locking pin in a retracted position. In its retracted or unlocked position, the front end of the flexion locking pin 32 is flush with the rotation locking member flange 27A and is disengaged from the holes 12C in the arcuate curved portion 12B at the back end of the quick disconnect connector 12.

When the flexion locking pin 32 is in its retracted position, the quick disconnect connector 12 may be manually pivoted about the pivot pin axis AT transverse to the longitudinal axis AL through an angle of from 0° to about 50° against the force of the tension spring 15. When the quick disconnect connector 12 is released, the force of the tension spring 15 returns it to the normally straight position with its cavity 12A parallel with the longitudinal axis AL of the wrist unit 10. When the quick disconnect connector 12 is being manually pivoted about the pivot pin axis AT, one of the holes 12C in the arcuate curved portion 12B at its back end may be positioned to receive the front end of the retractable flexion locking pin 32 when it is released by a second pull/relax action.

To release the retractable flexion locking pin 32 from its retracted position to its locking position, it is moved rearward against the force of the spring 33 by tensioning (pulling) and then relaxing the flexion control cable 34 a second time (second pull/relax action). During the second pull stroke, the flexion locking pin 32 and its cam groove 32A again moves rearward and rotates to a position so as to disengage the set screw from the stop surface of the cam groove, and on the relax stroke the flexion locking pin is urged forward by the force of the spring 33 to again assume its fully forward extended position engaged in one of the selected holes 12C in the arcuate curved portion 12B at the back end of the quick disconnect connector 12.

Thus, the quick disconnect connector 12 may be locked in one of three locking positions relative to the longitudinal axis AL of the wrist unit 10, and conical front member 11 carrying the quick disconnect connector 21, may be rotated as a unit and locked at any of a plurality of indexed locking positions about the longitudinal axis AL.

The phrase "terminal device" has been used throughout this disclosure referring to items that may be releasably connected to the prosthetic wrist unit by attaching them in the cavity 12A of the quick disconnect connector 12. Such terminal devices have an end portion that is adapted to be received in the cylindrical cavity 12A of the quick disconnect connector 12 and held therein by the detent ball and plunger mechanism 13. In a preferred embodiment, the proximal end of the terminal device TD is attached to a cylindrical insert or adapter 40 that is received in the cavity 12A and engaged by the detent ball and plunger mechanism 13. A suitable commercially available insert known as a "Quick Disconnect Insert" is manufactured by Texas Assistive Devices of Brazoria, Tex., and distributed by the Hosmer Dorrance Corporation of Campbell, Calif. This insert is an internally threaded cylindrical fitting which may be attached to various terminal devices and has a plurality of circumferential radially spaced holes 41 through its side wall which allows the terminal device to be selectively positioned at various rotated positions about the axis of the cavity 12A to provide still further selective positioning of the terminal device. It should be understood that terminal devices may be provided with a cylindrical end portion that is received in the cylindrical cavity of the present quick disconnect connector, and that other types of easily released terminal device retaining means may be used.

It should also be understood that a very wide variety of terminal devices may be provided for use with the present wrist unit, such as hooks, electric hands, tools, implements, and other specialty terminal devices. Typical examples of such specialty terminal devices include: personal care items (toothbrush, hairbrush, comb, etc.); kitchen utensils (knife, fork, spoon, whisk, spatula, etc); mechanic and carpentry tools (hammer, wrench, screwdriver, pliers, file, saw, nail holder, etc.); sporting and outdoor gear (fishing rod, reel crank adapter, golf club shank adapter, etc.) and gardening tools (spade, hoe, rake, etc.).

Although the wrist unit has been shown and described for purposes of example, as having a pair of cable operated locking pins, one for locking the front member at selected pronation and supination rotation positions, and a second for locking the quick disconnect connection at selected flexion and extension positions, it should be understood that other types of easily released locking means may be used. For example, the wrist unit may be provided with a single cable operated locking pin for locking the front member at selected pronation and supination rotation positions, as described above, and a pivoting lever locking member which releasably engages locking holes or notches in the arcuate curved portion 12B at the back end of the quick disconnect connector 12 to control the flexion and extension functions. In another example, the wrist unit may be provided a first pivoting lever locking member which releasably engages locking recesses in the rotation locking member sleeve for locking the front member at selected pronation and supination rotation positions, and a second pivoting lever locking member which releasably engages locking holes or notches in the arcuate curved portion 12B at the back end of the quick disconnect connector 12 to control the flexion and extension functions.

It should also be understood that a passageway may be formed through the back end of the cavity 12A of the quick disconnect connector 12 and passageways may be formed through the front and rear members for receiving an electrical cable such that electrically operated or myoelectric terminal devices such as hooks, electric hands, other specialty terminal devices may be attached and operatively connected through the wrist unit.

While this invention has been described fully and completely with special emphasis upon preferred embodiments, it should be understood that within the scope of the appended claims the invention may be practiced otherwise than as specifically described herein.

What we claim is:

1. A method for positioning a prosthetic terminal device at desired orientations with respect to the distal end of an arm prosthesis to perform useful functions, comprising the steps of:

providing a prosthetic wrist unit having a back section adapted to receive the distal end of an arm prosthesis, a front section rotatably connected with said back section to rotate relative thereto about a longitudinal axis extending through said arm prosthesis, rotary positioning means on said front section and releasable rotation locking means on said back section engageable with said rotary positioning means to lock said front section at a selected rotated position with respect to the longitudinal axis, quick disconnect connection means pivotally mounted on said front section to pivot about a transverse axis with respect to the longitudinal axis and having a receptacle at a distal end for releasable attachment of a terminal device thereto, angular positioning means on said quick disconnect connection means and flexion locking means on said wrist unit engageable with said angular positioning means to lock said quick disconnect connection means at a selected angular flexion or extension orientation about the transverse axis with respect to the longitudinal axis;

releasably attaching a terminal device to said quick disconnect connection means;

positioning and releasably locking said front section of said wrist unit and attached terminal device at a desired rotated pronation or supination orientation with respect to the longitudinal axis; and positioning and releasably locking said quick disconnect connection means and attached terminal device at a desired angular flexion or extension orientation about the transverse axis with respect to the longitudinal axis; whereby the terminal device is selectively positioned at a desired pronation or supination orientation and a desired angular flexion or extension orientation with respect to the distal end of the arm prosthesis and manipulated to perform useful functions.

2. The method according to claim 1, wherein said flexion locking means comprises a retractable spring loaded flexion locking element mounted on said wrist unit, and said angular positioning means comprises a plurality of radially spaced apertures at a proximal end of quick disconnect connection means disposed in an arcuate pattern about the transverse axis; and said step of releasably locking said quick disconnect connection means is accomplished by moving said flexion locking element to a spring biased locking position releasably engaged with a selected one of said radially spaced apertures;

said flexion locking element being movable to a retracted position disengaged from said selected one of said radially spaced apertures to allow pivotal movement of said quick disconnect connection means.

3. The method according to claim 2, wherein a flexion control cable is connected with said flexion locking element; and said flexion locking element is moved to its said retracted position by tensioning said flexion control cable, and is moved to its said locking position engaged with a selected one of said radially spaced apertures by releasing the tension in said flexion control cable.

4. The method according to claim 3, wherein said wrist unit further comprises retaining means operatively connected with said flexion locking element; and said step of moving said flexion locking element to its said retracted position is accomplished by tensioning and releasing tension in said flexion control cable a first time to retain said flexion locking element its said retracted position, and is moved to its said locking position engaged with a selected one of said radially spaced apertures by tensioning and releasing tension in said flexion control cable a second time.

5. The method according to claim 2, wherein said quick disconnect connection means is pivotal through a range of from 0° to more than 45° about the transverse axis, said wrist unit further comprises tension spring means operatively connected with said quick disconnect connection means; and said step of moving said flexion locking element to its said retracted position allows said tension spring means to return said quick disconnect connection means to a position wherein its said receptacle is in a plane parallel with the longitudinal axis.

6. The method according to claim 1, wherein said rotary positioning means has a plurality of equally spaced apart apertures disposed in a circular pattern;

said rotation locking means is a retractable spring loaded rotation locking element mounted on said back section; and said step of releasably locking said front section is accomplished by moving said rotation locking element to a spring biased locking position engaged with a selected one of said spaced apart apertures;

said rotation locking element being movable to a retracted position disengaged from said said selected one of said spaced apart apertures to allow rotation of said front section.

7. The method according to claim 6, wherein said wrist unit further comprises torsion spring means operatively connected with said rotary positioning means, and stop means disposed between said back section and said rotary positioning means;

said front section and said rotary positioning means are rotatable as a unit about the longitudinal axis through a range exceeding 270° in a clockwise or counter clockwise direction; and said step of moving said rotation locking element to its said retracted position allows said torsion spring means to return said front section and said rotary positioning means as a unit to a predetermined stop position engaged with said stop means.

8. The method according to claim 6, wherein a rotation control cable is connected with said rotation locking element; and said rotation locking element is moved to its said retracted position by tensioning said rotation control cable, and is moved to its said locking position engaged with a selected one of said spaced apart apertures by releasing the tension in said rotation control cable.

9. The method according to claim 8, wherein said wrist unit further comprises retaining means operatively connected with said rotation locking element; and said step of moving said rotation locking element to its said retracted position is accomplished by tensioning and releasing tension in said rotation control cable a first time to retain said rotation locking element its said retracted position, and is moved to its said locking position engaged with a selected one of said spaced apart apertures by tensioning and releasing tension in said rotation control cable a second time.

10. A multi-function body-powered prosthetic wrist unit for attachment to the distal end of an arm prosthesis for receiving a prosthetic terminal device and positioning the terminal device at desired orientations with respect to the arm prosthesis, comprising:
    a back section adapted to be releasably attached to the distal end of an arm prosthesis;
    a front section rotatably connected with said back portion to rotate relative thereto about a longitudinal axis extending through the arm prosthesis;
    quick disconnect connection means pivotally mounted on said front section to pivot about a transverse axis with respect to the longitudinal axis and having a receptacle for releasably attaching a terminal device thereto;
    rotary positioning means connected with said front section for selectively positioning said front section and the attached terminal device to a desired rotated pronation or supination orientation with respect to the longitudinal axis, and rotation locking means on said back section engageable with said rotary positioning means for releasably locking said front section at a selected rotated orientation about the longitudinal axis;
    angular positioning means connected with said quick disconnect connection means for selectively positioning said connection means and the attached terminal device to a desired angular flexion or extension orientation with respect to the transverse axis, and flexion locking means on said wrist unit engageable with said angular positioning means for releasably locking said connection means and the attached terminal device at a selected angular orientation about the transverse axis with respect to the longitudinal axis; whereby
    the attached terminal device is selectively positioned at desired angular flexion or extension orientation and a desired pronation or supination orientation with respect to the distal end of the arm prosthesis and manipulated to perform useful functions.

11. The prosthetic wrist unit according to claim 10, wherein
    said angular positioning means has a plurality of radially spaced apertures in an arcuate pattern about the transverse axis; and
    said flexion locking means is a retractable spring loaded flexion locking element mounted on said wrist unit for movement between a locking position engaged with a selected one of said radially spaced apertures and a retracted position disengaged therefrom;
    said flexion locking element in its retracted position allowing pivotal movement of said quick disconnect connection means to the desired angular flexion or extension orientation about the transverse axis, and in its locking position being spring biased into engagement with one of said radially spaced apertures.

12. The prosthetic wrist unit according to claim 11, further comprising:
    a flexion control cable connected with said flexion locking element whereby said flexion locking element is moved to its said retracted position by tensioning said flexion control cable, and is moved to its said locking position engaged with a selected one of said radially spaced apertures by releasing the tension in said flexion control cable.

13. The prosthetic wrist unit according to claim 12, further comprising:
    retaining means operatively connected with said flexion locking element to retain said flexion locking element in its said retracted position by tensioning and releasing tension in said flexion control cable a first time, and is moved to its said locking position engaged with a selected one of said radially spaced apertures by tensioning and releasing tension in said flexion control cable a second time.

14. The prosthetic wrist unit according to claim 11, wherein
    said quick disconnect connection means is pivotal through a range of from 0° to more than 45° about the transverse axis; and further comprising
    tension spring means operatively connected with said quick disconnect connection means for returning said connection means to a position wherein its said receptacle is in a plane parallel with the longitudinal axis when said flexion locking element is in its said retracted position.

15. The prosthetic wrist unit according to claim 10, wherein
    said rotary positioning means has a plurality of equally spaced apart apertures in a circular pattern; and
    said rotation locking means is a retractable spring loaded rotation locking element mounted on said back section for movement between a locking position engaged with a selected one of said spaced apart apertures and a retracted position disengaged therefrom;
    said rotation locking element in its retracted position allowing rotation of said front section and said rotary positioning means as a unit to the desired rotated pronation or supination orientation, and in its locking position being spring biased into engagement with one of said spaced apart apertures.

16. The prosthetic wrist unit according to claim 15, further comprising:
    stop means disposed between said back section and said rotary positioning means for allowing rotation of said front section and said rotary positioning means as a unit about the longitudinal axis through a range exceeding 270° in a clockwise or counter clockwise direction; and
    torsion spring means operatively connected with said rotary positioning means for returning said rotary positioning means to a predetermined stop position.

17. The prosthetic wrist unit according to claim 15, further comprising:
    a rotation control cable connected with said rotation locking element whereby said rotation locking element is moved to its said retracted position by tensioning said rotation control cable, and is moved to its said locking position engaged with a selected one of said spaced apart apertures by releasing the tension in said rotation control cable.

18. The prosthetic wrist unit according to claim 17, further comprising:
    retaining means operatively connected with said rotation locking element to retain said rotation locking element in its said retracted position by tensioning and releasing tension in said rotation control cable a first time, and is moved to its said locking position engaged with a selected one of said spaced apart apertures by tensioning and releasing tension in said rotation control cable a second time.

* * * * *